US00PP23989P3

(12) United States Plant Patent
Fransen

(10) Patent No.: US PP23,989 P3
(45) Date of Patent: Oct. 15, 2013

(54) *HOSTA* PLANT NAMED 'HANDS UP'

(50) Latin Name: ***Hosta* hybrid**
Varietal Denomination: Hands Up

(75) Inventor: Marco Fransen, Tel Aar (NL)

(73) Assignee: Vernooij V.O.F. (NL)

( * ) Notice: Subject to any disclaimer, the term of this patent is extended or adjusted under 35 U.S.C. 154(b) by 1 day.

(21) Appl. No.: 13/135,822

(22) Filed: Jul. 14, 2011

(65) Prior Publication Data

US 2013/0019361 P1 Jan. 17, 2013

(51) Int. Cl.
*A01H 5/00* (2006.01)

(52) U.S. Cl.
USPC ..... Plt./353

(58) Field of Classification Search
USPC ..... Plt./353
See application file for complete search history.

*Primary Examiner* — June Hwu
(74) *Attorney, Agent, or Firm* — Cassandra Bright

(57) ABSTRACT

A new and distinct *Hosta* cultivar named 'Hands Up' is disclosed, characterized by a distinctive upright plant habit, large flowers, vigorous plant habit and strong foliage, with good resistance to environmental stressors. The near variety is a *Hosta*, typically used for outdoor ornamental purposes.

1 Drawing Sheet

Latin name of the genus and species: *Hosta* hybrid.
Variety denomination: 'HANDS UP'.

BACKGROUND OF THE INVENTION

The new cultivar was discovered as an induced mutation using the known chemical colchicine, of *Hosta* hybrid 'Praying Hands' unpatented. 'Hands Up' was discovered by the inventor, Marco Fransen, a citizen of the Netherlands in October of 2008, at a research facility in Ter Aar, The Netherlands. The intent of the breeding program was to create new tetraploid *Hosta* hyrids with stronger foliage and plant vigor.

Directly after discovery of the tetraploid mutation, the inventor initiated cultivation in tissue culture, during October of 2008, in a commercial laboratory in Iribov Heerhugowaard, the Netherlands. 'Hands Up' was first propagated in the same commercial laboratory in Iribov Heerhugowaard, the Netherlands by tissue culture. Subsequently 'Hands Up' has been reproduced by micro-propagation and has shown that the unique features of this cultivar are stable and reproduced true to type through several generations.

SUMMARY OF THE INVENTION

The cultivar 'Hands Up' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Hands Up' These characteristics in combination distinguish 'Hands Up' as a new and distinct *Hosta* cultivar:

1. Distinctive, upright plant habit.
2. Thick foliage.
3. Large flowers.
4. Vigorous plant.

COMPARISON TO PARENT

Plants of the new cultivar 'Hands Up' are similar to plants of the parent; *Hosta* hybrid 'Praying Hands' in most horticultural characteristics, however, plants of the new cultivar 'Hands Up' are more vigorous and produce thicker, stronger leaves than the parent variety. Additionally, the new variety produces larger flowers than 'Praying Hands'. Leaves of 'Hands Up' have a wider variegation on the margin than 'Praying Hands'.

COMMERCIAL COMPARISON

The most similar commercial *Hosta* hybrid variety available to compare to 'Hands Up' is the parent variety, as the very strong upright habit is not commonly found in *Hostas*.

BRIEF DESCRIPTION OF THE PHOTOGRAPH

The accompanying photograph in FIG. 1 illustrates in full color a typical plant of 'Hands Up' grown outdoors. This plant is approximately 6 months old, shown in a 1 liter pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001, except where general terms of ordinary dictionary significance are used. The following observations and measurements describe 'Hands Up' plants grown in a commercial nursery in the Netherlands, from February of 2011 through June of 2011. Temperatures were 5° C. to 20° C. at night and 10° C. to 30° C. during the day. Measurements and numerical values represent averages of typical plant types. No growth regulators or special treatments were used.

Botanical classification: *Hosta* hybrid 'Hands Up'.

PROPAGATION

Time to initiate roots: Approximately 14 to 21 days at 23° C.
Root description: Fleshy with moderate side roots.

PLANT

Growth habit: Upright, herbaceous perennial plant.
Height: Approximately 29 cm in a 1 liter pot.
Plant spread: Approximately 20 cm.
Growth rate: Moderate.
Branching characteristics: Branches emerge directly from the roots.
Age of plant described: Approximately 4 months from a stage 3 tissue culture.

FOLIAGE

Leaf:
- *Quantity per plant.*—Average 50.
- *Leaf type.*—Simple, basal emerging.
- *Average leaf length.*—Approximately 22 cm.
- *Average leaf width.*—Approximately 9.7 cm.
- *Apex.*—Acute.
- *Base.*—Attenuate.
- *Overall leaf shape.*—Lanceolate to lanceolate-oblong.
- *Overall leaf aspect.*—Slightly arching, undulating.
- *Margin.*—Wavy.
- *Texture of top surface.*—Smooth.
- *Texture of bottom surface.*—Smooth.
- *Appearance of top surface.*—Slightly leathery.
- *Appearance of bottom surface.*—Slightly leathery.
- *Pubescence.*—No pubescence on leaves.
- *Color.*—Young foliage upper side: Near RHS Green 137A, margin near RHS Yellow-Green 151A. Young foliage under side: Near RHS Green 137A, margin near RHS Yellow-Green 151A. Mature foliage upper side: Near RHS Green 137A, margin near RHS Yellow-Green 151A. Mature foliage under side: Near RHS Green 137A, margin near RHS Yellow-Green 151A.
- *Venation.*—Type: Pinnate. Venation coloration upper side: Near RHS Green 137B. Venation coloration under side: Near RHS Green 137B.

Leaf petiole:
- *Length.*—Approximately 8.4 cm.
- *Width.*—Approximately 2.5 cm.
- *Color.*—Upper side: Near RHS Green 137B. Under side: Near RHS Green 137B.
- *Strength.*—Very strong.

Other foliage characteristics: Thick foliage, resistant to mechanical damage and environmental stressors.

FLOWER

Natural flowering season: Late Spring into Summer.
Inflorescence type and habit: Typically — Single, campanulate arranged in racemes.
Rate of flower opening: Lowest flower opens first, all flowers have opened in approx. 2 weeks.
Flower longevity on plant: Approx. 2 weeks.
Quantity of flowers: Average: 9 flowers per raceme.
Raceme size:
- *Height.*—Approximately 14.7 cm, from lowest flower to top of Inflorescence.
- *Width.*—Approximately 5.6 cm.

Flower:
- *Perianth.*—Arrangement: Campanulate.
- *Overall flower size.*—Length: Approximately 5.3 cm. Width: Approximately 2.1 cm at widest point.

Color:
- *Tepals.*—When opening: Outer surface: Near RHS Violet 85D, tinged near RHS Violet 85C. Inner surface: Near RHS Violet 85B, base near RHS N155A, tube color RHS Violet 85C.
- *Fully opened.*—Outer surface: Near RHS Violet 85D. Inner surface: Near RHS 85B, base near RHS N155A, tube near RHS 85D. Color Changes when Aging: Near RHS Violet 85D.

Sepals or bracts:
- *Quantity.*—One bract is placed under each individual flower.
- *Shape.*—Ovate, strongly concave.
- *Length.*—Approximately 1.9 cm.
- *Diameter.*—Approximately 0.4 cm.
- *Color.*—Outer surface: Near RHS Green 143C, base near RHS Yellow-Green 144D. Inner surface: Near RHS 143C. Color Changes when Aging: Near RHS Greyed-Orange 164B.

Bud:
- *Shape.*—Obovate.
- *Length.*—Approximately 2.3 cm.
- *Diameter.*—Approximately 0.7 cm.
- *Color.*—Near RHS Violet 85D.

Pedicels:
- *Length.*—Approximately 0.5 cm.
- *Width.*—Approximately 0.2 cm.
- *Aspect.*—Placed to the petiole in an average angle of 30° (0°=horizontal), curved downward in an average angle of 20° (0°=horizontal).
- *Color.*—Near RHS Violet 85D.

Scape:
- *Length.*—Approximately 14.5 cm.
- *Width.*—Approximately 0.3 cm.
- *Angle.*—Near vertical.
- *Strength.*—Strong.
- *Color.*—Near RHS Yellow-Green 144A, covered with a thin waxy layer, near RHS Greyed-Green 190C.

Fragrance: No.

REPRODUCTIVE ORGANS

Stamens:
- *Number.*—Average 6.
- *Filament length.*—Approximately 5.0 cm.
- *Filament color.*—Near RHS Yellow-Green 145D.
- *Anther length.*—Approximately 0.5 cm.
- *Anther color.*—Near RHS Greyed-Orange 176C.
- *Anther shape.*—Oblong, dorsifixed.
- *Pollen.*—: Moderate, colored near RHS Yellow-Orange 17A.

Pistil:
- *Number.*—1.
- *Length.*—Approximately 5.74 cm.

*Style color.*—Near RHS Greyed-Green 157C, base near Yellow-Green 145D.

*Stigma.*—Shape: Club-shaped. Color: Near RHS White N155D.

*Ovary color.*—Near RHS Yellow-Green 145A.

OTHER CHARACTERISTICS

Fruits and seeds: The new variety has not been observed to produce fruits or seeds to date.

Disease resistance: Better resistance to diseases or pests has been observed in this variety, due to the strong, thick foliage.

Temperature tolerance: Hardy perennial, tolerates a temperature range from approximately −30° C. to at least 40° C.

Drought tolerance: No tolerance for drought.

What is claimed is:

1. A new and distinct cultivar of *Hosta* plant named 'Hands Up' as herein illustrated and described.

* * * * *

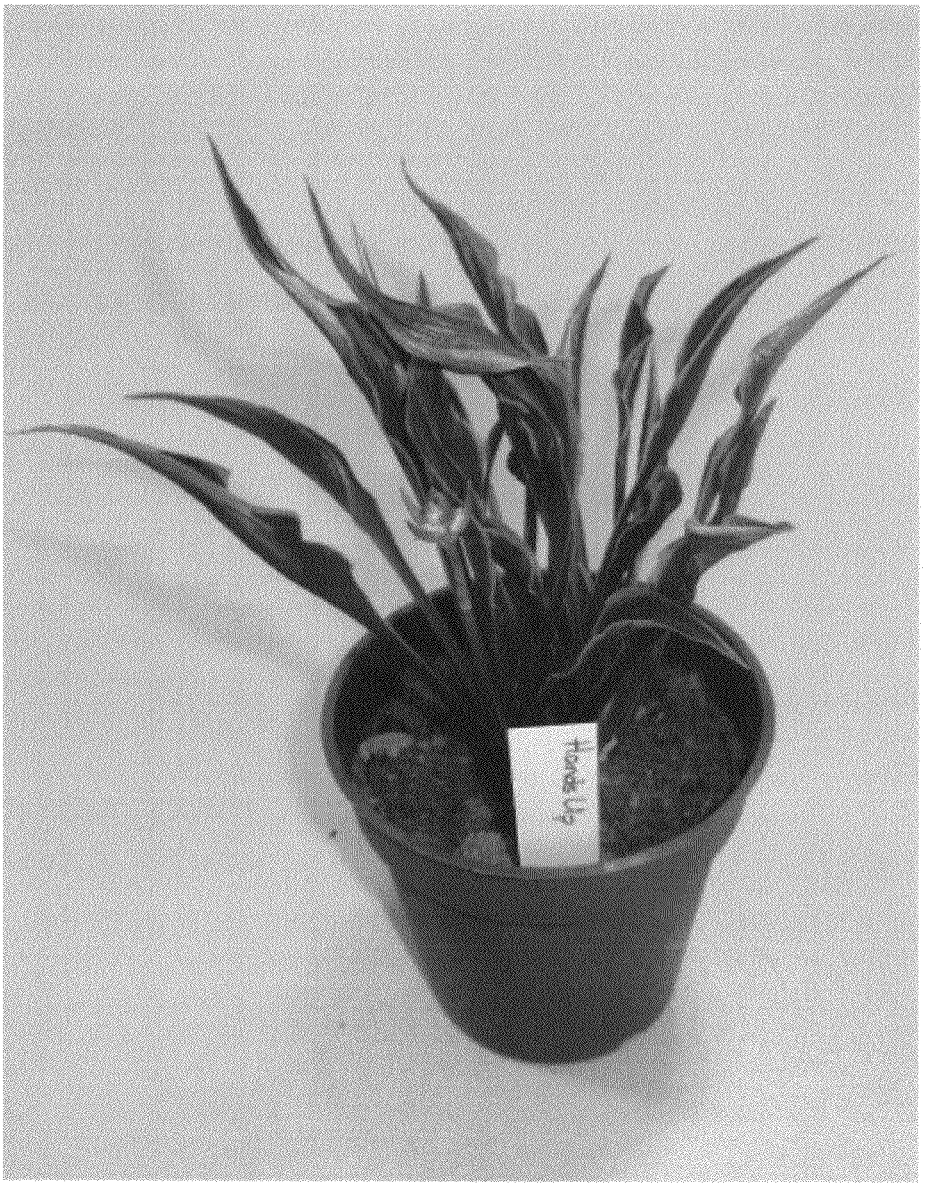
Hosta Up